(12) United States Patent
Falkel

(10) Patent No.: US 12,150,831 B2
(45) Date of Patent: Nov. 26, 2024

(54) COMBINED ORTHODONTIC MOVEMENT OF TEETH WITH COSMETIC RESTORATION

(71) Applicant: uLab Systems, Inc., Menlo Park, CA (US)

(72) Inventor: Michael I. Falkel, Carmel, CA (US)

(73) Assignee: uLab Systems, Inc., Memphis, TN (US)

(*) Notice: Subject to any disclaimer, the term of this patent is extended or adjusted under 35 U.S.C. 154(b) by 0 days.

(21) Appl. No.: 15/710,703

(22) Filed: Sep. 20, 2017

(65) Prior Publication Data

US 2018/0078335 A1  Mar. 22, 2018

Related U.S. Application Data

(60) Provisional application No. 62/397,783, filed on Sep. 21, 2016.

(51) Int. Cl.
*A61C 7/00* (2006.01)
*A61C 5/20* (2017.01)
(Continued)

(52) U.S. Cl.
CPC ............... *A61C 7/002* (2013.01); *A61C 5/20* (2017.02); *A61C 5/77* (2017.02); *A61C 7/08* (2013.01); *A61C 9/004* (2013.01); *A61C 13/0004* (2013.01); *G16H 20/30* (2018.01); *G16H 20/40* (2018.01); *G16H 50/20* (2018.01); *G16H 50/50* (2018.01)

(58) Field of Classification Search
CPC .. A61C 7/002; A61C 7/08; A61C 5/20; A61C 5/77; A61C 13/0004
See application file for complete search history.

(56) References Cited

U.S. PATENT DOCUMENTS

| 3,521,355 A | 7/1970 | Pearlman |
| 4,068,379 A | 1/1978 | Miller et al. |

(Continued)

FOREIGN PATENT DOCUMENTS

| CA | 2557573 | 7/2012 |
| CN | 1575782 | 2/2005 |

(Continued)

OTHER PUBLICATIONS

Kovach, I. V. et al., "Clinic, diagnosis, treatment, prevention, prosthetics various dentofacial anomalies and deformities," DMA, 2018.

*Primary Examiner* — Edward Moran
(74) *Attorney, Agent, or Firm* — Levine Bagade Han LLP

(57) ABSTRACT

Systems and methods are disclosed for restoring and/or orthodontically moving teeth. The methods can include determining an orthodontic treatment plan to at least partially correct for a malocclusion of at least one tooth. The methods can include determining an amount of cosmetic restoration of the at least one tooth based on a degree of partial correction of the malocclusion. The methods can include preparing the at least one tooth for the cosmetic restoration by orthodontically moving the tooth from a first position to a second position. The methods can include cosmetically restoring the at least one tooth when the at least one tooth is in the second position.

11 Claims, 4 Drawing Sheets

(51) Int. Cl.
  *A61C 5/77* (2017.01)
  *A61C 7/08* (2006.01)
  *A61C 9/00* (2006.01)
  *A61C 13/00* (2006.01)
  *G16H 20/30* (2018.01)
  *G16H 20/40* (2018.01)
  *G16H 50/20* (2018.01)
  *G16H 50/50* (2018.01)

(56) References Cited

U.S. PATENT DOCUMENTS

| | | |
|---|---|---|
| 4,889,485 A | 12/1989 | Iida |
| 4,983,334 A | 1/1991 | Adell |
| 5,055,039 A | 10/1991 | Abbatte et al. |
| 5,186,623 A | 2/1993 | Breads et al. |
| 5,259,762 A | 11/1993 | Farrell |
| 5,506,607 A | 4/1996 | Sanders et al. |
| 5,691,905 A | 11/1997 | Dehoff et al. |
| 5,863,198 A | 1/1999 | Doyle |
| 5,975,893 A | 11/1999 | Chishti et al. |
| 6,183,248 B1 | 2/2001 | Chishti et al. |
| 6,210,162 B1 | 4/2001 | Chishti et al. |
| 6,217,325 B1 | 4/2001 | Chishti et al. |
| 6,227,850 B1 | 5/2001 | Chishti et al. |
| 6,227,851 B1 | 5/2001 | Chishti et al. |
| 6,250,918 B1 | 6/2001 | Sachdeva et al. |
| 6,293,790 B1 | 9/2001 | Hilliard |
| 6,299,440 B1 | 10/2001 | Phan et al. |
| 6,309,215 B1 | 10/2001 | Phan et al. |
| 6,315,553 B1 | 11/2001 | Sachdeva et al. |
| 6,386,878 B1 | 5/2002 | Pavlovskaia et al. |
| 6,390,812 B1 | 5/2002 | Chishti et al. |
| 6,394,801 B2 | 5/2002 | Chishti et al. |
| 6,398,548 B1 | 6/2002 | Chishti et al. |
| 6,454,565 B2 | 9/2002 | Phan et al. |
| 6,463,344 B1 | 10/2002 | Pavloskaia |
| 6,471,511 B1 | 10/2002 | Chishti et al. |
| 6,485,298 B2 | 11/2002 | Chishti et al. |
| 6,488,499 B1 | 12/2002 | Miller |
| 6,524,101 B1 | 2/2003 | Phan et al. |
| 6,554,611 B2 | 4/2003 | Chishti et al. |
| 6,572,372 B1 | 6/2003 | Phan et al. |
| 6,582,227 B2 | 6/2003 | Phan et al. |
| 6,602,070 B2 | 8/2003 | Miller et al. |
| 6,607,382 B1 | 8/2003 | Kuo et al. |
| 6,626,666 B2 | 9/2003 | Chishti et al. |
| 6,629,840 B2 | 10/2003 | Chishti et al. |
| 6,682,346 B2 | 1/2004 | Chishti et al. |
| 6,688,885 B1 | 2/2004 | Sachdeva |
| 6,699,037 B2 | 3/2004 | Chishti et al. |
| 6,702,575 B2 | 3/2004 | Hilliard |
| 6,705,861 B2 | 3/2004 | Chishti et al. |
| 6,705,863 B2 | 3/2004 | Phan et al. |
| 6,722,880 B2 | 4/2004 | Chishti et al. |
| 6,729,876 B2 | 5/2004 | Chishti et al. |
| 6,761,560 B2 | 7/2004 | Miller |
| 6,783,360 B2 | 8/2004 | Chishti |
| 6,786,721 B2 | 9/2004 | Chishti et al. |
| 6,802,713 B1 | 10/2004 | Chishti et al. |
| 6,830,450 B2 | 12/2004 | Knopp et al. |
| 6,846,179 B2 | 1/2005 | Chapouland et al. |
| 6,857,429 B2 | 2/2005 | Eubank |
| 6,886,566 B2 | 5/2005 | Eubank |
| 6,964,564 B2 | 11/2005 | Phan et al. |
| 7,011,517 B2 | 3/2006 | Nicozisis |
| 7,029,275 B2 | 4/2006 | Rubbert et al. |
| 7,037,108 B2 | 5/2006 | Chishti et al. |
| 7,040,896 B2 | 5/2006 | Pavlovskaia et al. |
| 7,056,115 B2 | 6/2006 | Phan et al. |
| 7,059,850 B1 | 6/2006 | Phan et al. |
| 7,063,533 B2 | 6/2006 | Phan et al. |
| 7,074,038 B1 | 7/2006 | Miller |
| 7,077,647 B2 | 7/2006 | Choi et al. |
| 7,092,784 B1 | 8/2006 | Simkins |
| 7,104,790 B2 | 9/2006 | Cronauer |
| 7,121,825 B2 | 10/2006 | Chishti et al. |
| 7,125,248 B2 | 10/2006 | Phan et al. |
| 7,134,874 B2 | 11/2006 | Chishti et al. |
| 7,156,661 B2 | 1/2007 | Choi et al. |
| 7,160,110 B2 | 1/2007 | Imgrund et al. |
| 7,172,417 B2 | 2/2007 | Sporbert et al. |
| 7,192,275 B2 | 3/2007 | Miller |
| 7,220,122 B2 | 5/2007 | Chishti |
| 7,320,592 B2 | 1/2008 | Chishti et al. |
| 7,326,051 B2 | 2/2008 | Miller |
| 7,331,783 B2 | 2/2008 | Chishti et al. |
| 7,347,688 B2 | 3/2008 | Kopelman et al. |
| 7,416,407 B2 | 8/2008 | Cronauer |
| 7,434,582 B2 | 10/2008 | Eubank |
| 7,435,083 B2 | 10/2008 | Chishti et al. |
| 7,442,041 B2 | 10/2008 | Imgrund et al. |
| 7,458,812 B2 | 12/2008 | Sporbert et al. |
| 7,476,100 B2 | 1/2009 | Kuo |
| 7,553,157 B2 | 6/2009 | Abolfathi et al. |
| 7,559,328 B2 | 7/2009 | Eubank |
| 7,578,673 B2 | 8/2009 | Wen et al. |
| 7,590,462 B2 | 9/2009 | Rubbert et al. |
| 7,637,262 B2 | 12/2009 | Bailey |
| 7,641,828 B2 | 1/2010 | Desimone et al. |
| 7,658,610 B2 | 2/2010 | Knopp |
| 7,689,398 B2 | 3/2010 | Cheng et al. |
| 7,717,708 B2 | 5/2010 | Sachdeva et al. |
| 7,771,195 B2 | 8/2010 | Knopp et al. |
| 7,802,987 B1 | 9/2010 | Phan et al. |
| 7,824,180 B2 | 11/2010 | Abolfathi et al. |
| 7,826,646 B2 | 11/2010 | Pavlovskaia et al. |
| 7,840,247 B2 | 11/2010 | Liew et al. |
| 7,841,858 B2 | 11/2010 | Knopp et al. |
| 7,845,938 B2 | 12/2010 | Kim et al. |
| 7,854,609 B2 | 12/2010 | Chen et al. |
| 7,878,801 B2 | 2/2011 | Abolfathi et al. |
| 7,878,804 B2 | 2/2011 | Korytov et al. |
| 7,878,805 B2 | 2/2011 | Moss et al. |
| 7,883,334 B2 | 2/2011 | Li et al. |
| 7,901,207 B2 | 3/2011 | Knopp et al. |
| 7,905,724 B2 | 3/2011 | Kuo et al. |
| 7,914,283 B2 | 3/2011 | Kuo |
| 7,942,672 B2 | 5/2011 | Kuo |
| 7,943,079 B2 | 5/2011 | Desimone et al. |
| 7,957,824 B2 | 6/2011 | Boronvinskih et al. |
| 7,987,099 B2 | 7/2011 | Kuo et al. |
| 8,001,972 B2 | 8/2011 | Eubank |
| 8,002,543 B2 | 8/2011 | Kang et al. |
| 8,021,147 B2 | 9/2011 | Sporbert et al. |
| 8,033,282 B2 | 10/2011 | Eubank |
| 8,038,444 B2 | 10/2011 | Kitching et al. |
| 8,070,487 B2 | 12/2011 | Chishti et al. |
| 8,075,306 B2 | 12/2011 | Kitching et al. |
| 8,099,268 B2 | 1/2012 | Kitching et al. |
| 8,099,305 B2 | 1/2012 | Kuo et al. |
| 8,105,080 B2 | 1/2012 | Chishti et al. |
| 8,123,519 B2 | 2/2012 | Schultz |
| 8,152,518 B2 | 4/2012 | Kuo |
| 8,152,523 B2 | 4/2012 | Sporbert et al. |
| 8,177,551 B2 | 5/2012 | Sachdeva et al. |
| 8,235,713 B2 | 8/2012 | Phan et al. |
| 8,272,866 B2 | 9/2012 | Chun et al. |
| 8,275,180 B2 | 9/2012 | Kuo et al. |
| 8,292,617 B2 | 10/2012 | Brandt et al. |
| 8,303,302 B2 | 11/2012 | Teasdale |
| 8,348,665 B2 | 1/2013 | Kuo |
| 8,356,993 B1 | 1/2013 | Marston |
| 8,401,686 B2 | 3/2013 | Moss et al. |
| 8,401,826 B2 | 3/2013 | Cheng et al. |
| 8,439,672 B2 | 5/2013 | Matov et al. |
| 8,439,673 B2 | 5/2013 | Korytov et al. |
| 8,444,412 B2 | 5/2013 | Baughman et al. |
| 8,465,280 B2 | 6/2013 | Sachdeva et al. |
| 8,469,705 B2 | 6/2013 | Sachdeva et al. |
| 8,469,706 B2 | 6/2013 | Kuo |
| 8,496,474 B2 | 7/2013 | Chishti et al. |
| 8,512,037 B2 | 8/2013 | Andreiko |
| 8,517,726 B2 | 8/2013 | Kakavand et al. |

(56) References Cited

U.S. PATENT DOCUMENTS

| | | |
|---|---|---|
| 8,535,580 B2 | 9/2013 | Puttler et al. |
| 8,562,337 B2 | 10/2013 | Kuo et al. |
| 8,562,338 B2 | 10/2013 | Kitching et al. |
| 8,562,340 B2 | 10/2013 | Chishti et al. |
| 8,636,509 B2 | 1/2014 | Miller |
| 8,636,510 B2 | 1/2014 | Kitching et al. |
| 8,690,568 B2 | 4/2014 | Chapoulaud et al. |
| 8,708,697 B2 | 4/2014 | Li et al. |
| 8,734,149 B2 | 5/2014 | Phan et al. |
| 8,734,150 B2 | 5/2014 | Chishti et al. |
| 8,738,165 B2 | 5/2014 | Cinader, Jr. et al. |
| 8,765,031 B2 | 7/2014 | Li et al. |
| 8,777,611 B2 | 7/2014 | Cios |
| 8,780,106 B2 | 7/2014 | Chishti et al. |
| 8,807,999 B2 | 8/2014 | Kuo et al. |
| 8,858,226 B2 | 10/2014 | Phan et al. |
| 8,864,493 B2 | 10/2014 | Leslie-Martin et al. |
| 8,899,976 B2 | 12/2014 | Chen et al. |
| 8,899,978 B2 | 12/2014 | Kitching et al. |
| 8,930,219 B2 | 1/2015 | Trosien et al. |
| 8,936,464 B2 | 1/2015 | Kopelman |
| 8,998,608 B2 | 1/2015 | Trosien et al. |
| 8,944,812 B2 | 2/2015 | Kuo |
| 8,961,173 B2 | 2/2015 | Miller |
| 8,986,003 B2 | 3/2015 | Valoir |
| 8,992,215 B2 | 3/2015 | Chapoulaud et al. |
| 9,004,915 B2 | 4/2015 | Moss et al. |
| 9,022,781 B2 | 5/2015 | Kuo et al. |
| 9,026,238 B2 | 5/2015 | Kraemer et al. |
| 9,060,829 B2 | 6/2015 | Sterental et al. |
| 9,107,722 B2 | 8/2015 | Matov et al. |
| 9,119,691 B2 | 9/2015 | Namiranian et al. |
| 9,119,696 B2 | 9/2015 | Giordano et al. |
| 9,161,823 B2 | 10/2015 | Morton et al. |
| 9,161,824 B2 | 10/2015 | Chishti et al. |
| 9,204,942 B2 | 12/2015 | Phan et al. |
| 9,211,166 B2 | 12/2015 | Kuo et al. |
| 9,241,774 B2 | 1/2016 | Li et al. |
| 9,301,814 B2 | 4/2016 | Kaza et al. |
| 9,320,575 B2 | 4/2016 | Chishti et al. |
| 9,326,830 B2 | 5/2016 | Kitching et al. |
| 9,326,831 B2 | 5/2016 | Cheang |
| 9,333,052 B2 | 5/2016 | Miller |
| 9,345,557 B2 | 5/2016 | Anderson et al. |
| 9,351,809 B2 | 5/2016 | Phan et al. |
| 9,364,297 B2 | 6/2016 | Kitching et al. |
| 9,375,300 B2 | 6/2016 | Matov et al. |
| 9,414,897 B2 | 8/2016 | Wu et al. |
| 9,433,476 B2 | 9/2016 | Khardekar et al. |
| 9,492,245 B2 | 11/2016 | Sherwood et al. |
| 9,820,829 B2 | 11/2017 | Kuo |
| 9,844,420 B2 | 12/2017 | Cheang |
| 9,917,868 B2 | 3/2018 | Ahmed |
| 9,922,170 B2 | 3/2018 | Trosien et al. |
| 10,011,050 B2 | 7/2018 | Kitching et al. |
| 10,022,204 B2 | 7/2018 | Cheang |
| 10,335,250 B2 | 7/2019 | Wen |
| 10,357,336 B2 | 7/2019 | Wen |
| 10,357,342 B2 | 7/2019 | Wen |
| 10,548,690 B2 | 2/2020 | Wen |
| 10,588,723 B2 | 3/2020 | Falkel |
| 10,631,953 B2 | 4/2020 | Wen |
| 10,642,717 B2 | 4/2020 | Wen |
| 10,881,486 B2 | 1/2021 | Wen |
| 10,925,698 B2 | 2/2021 | Falkel |
| 10,952,821 B2 | 3/2021 | Falkel |
| 11,051,913 B2 | 7/2021 | Wen |
| 11,096,763 B2 | 8/2021 | Akopov et al. |
| 11,207,161 B2 | 12/2021 | Brant |
| 11,348,257 B2 | 5/2022 | Lang |
| 11,364,098 B2 | 6/2022 | Falkel |
| 11,553,989 B2 | 1/2023 | Wen et al. |
| 11,583,365 B2 | 2/2023 | Wen |
| 11,638,628 B2 | 5/2023 | Wen |
| 11,663,383 B2 | 5/2023 | Cao |
| 11,707,180 B2 | 7/2023 | Falkel |
| 11,771,524 B2 | 10/2023 | Wen |
| 11,833,006 B2 | 12/2023 | Wen |
| 12,064,315 B2 | 8/2024 | Schueller et al. |
| 2001/0002310 A1* | 5/2001 | Chishti .......... B33Y 80/00 433/24 |
| 2002/0009686 A1 | 1/2002 | Loc et al. |
| 2002/0010568 A1 | 1/2002 | Rubbert et al. |
| 2002/0025503 A1 | 2/2002 | Chapoulaud et al. |
| 2002/0042038 A1 | 4/2002 | Miller et al. |
| 2002/0051951 A1 | 5/2002 | Chishti et al. |
| 2002/0072027 A1 | 6/2002 | Chisti |
| 2002/0094503 A1 | 7/2002 | Chishti et al. |
| 2002/0110776 A1 | 8/2002 | Abels et al. |
| 2002/0150859 A1 | 11/2002 | Imgrund et al. |
| 2002/0177108 A1 | 11/2002 | Pavlovskaia et al. |
| 2003/0003416 A1 | 1/2003 | Chishti et al. |
| 2003/0008259 A1 | 1/2003 | Kuo et al. |
| 2003/0039940 A1 | 2/2003 | Miller |
| 2003/0059736 A1 | 3/2003 | Lai et al. |
| 2003/0190576 A1 | 10/2003 | Phan et al. |
| 2003/0207224 A1 | 11/2003 | Lotte |
| 2004/0023188 A1 | 2/2004 | Pavlovskaia et al. |
| 2004/0029068 A1 | 2/2004 | Sachdeva et al. |
| 2004/0038168 A1 | 2/2004 | Choi et al. |
| 2004/0134599 A1 | 7/2004 | Wang et al. |
| 2004/0142299 A1 | 7/2004 | Miller |
| 2004/0152036 A1 | 8/2004 | Abolfathi |
| 2004/0166456 A1 | 8/2004 | Chishti et al. |
| 2004/0166462 A1 | 8/2004 | Phan et al. |
| 2004/0166463 A1 | 8/2004 | Wen et al. |
| 2004/0197728 A1 | 10/2004 | Abolfathi et al. |
| 2004/0202983 A1 | 10/2004 | Tricca et al. |
| 2004/0219471 A1 | 11/2004 | Cleary et al. |
| 2004/0229183 A1 | 11/2004 | Knopp et al. |
| 2004/0242987 A1 | 12/2004 | Liew et al. |
| 2004/0253562 A1 | 12/2004 | Knopp |
| 2005/0010450 A1 | 1/2005 | Hultgren et al. |
| 2005/0019721 A1 | 1/2005 | Chishti |
| 2005/0048432 A1 | 3/2005 | Choi et al. |
| 2005/0095552 A1 | 5/2005 | Sporbert et al. |
| 2005/0095562 A1 | 5/2005 | Sporbert et al. |
| 2005/0118555 A1 | 6/2005 | Sporbert et al. |
| 2005/0153255 A1* | 7/2005 | Sporbert .......... A61C 7/00 433/24 |
| 2005/0192835 A1 | 9/2005 | Kuo et al. |
| 2005/0194022 A1 | 9/2005 | Schwartz |
| 2005/0238967 A1 | 10/2005 | Rogers et al. |
| 2005/0241646 A1 | 11/2005 | Sotos et al. |
| 2005/0244781 A1 | 11/2005 | Abels et al. |
| 2005/0244782 A1 | 11/2005 | Chishti et al. |
| 2005/0271996 A1 | 12/2005 | Sporbert et al. |
| 2006/0003283 A1 | 1/2006 | Miller et al. |
| 2006/0035197 A1 | 2/2006 | Hishimoto |
| 2006/0068353 A1 | 3/2006 | Abolfathi et al. |
| 2006/0078840 A1 | 4/2006 | Robson |
| 2006/0078841 A1 | 4/2006 | Desimone et al. |
| 2006/0084030 A1 | 4/2006 | Phan et al. |
| 2006/0093982 A1 | 5/2006 | Wen |
| 2006/0099546 A1 | 5/2006 | Bergersen |
| 2006/0115785 A1 | 6/2006 | Li et al. |
| 2006/0147872 A1 | 7/2006 | Andreiko |
| 2006/0177789 A1 | 8/2006 | O'Bryan |
| 2006/0188834 A1 | 8/2006 | Hilliard |
| 2006/0199142 A1 | 9/2006 | Liu et al. |
| 2006/0223022 A1 | 10/2006 | Solomon |
| 2006/0223023 A1 | 10/2006 | Lai et al. |
| 2006/0275731 A1 | 12/2006 | Wen et al. |
| 2006/0275736 A1* | 12/2006 | Wen .......... A61C 9/00 433/213 |
| 2007/0003907 A1 | 1/2007 | Chishti et al. |
| 2007/0238065 A1* | 10/2007 | Sherwood .......... A61C 7/08 433/24 |
| 2007/0264606 A1 | 11/2007 | Muha et al. |
| 2007/0283967 A1 | 12/2007 | Bailey |
| 2008/0032248 A1 | 2/2008 | Kuo |
| 2008/0044786 A1 | 2/2008 | Kalili |
| 2008/0050692 A1 | 2/2008 | Hilliard |
| 2008/0051650 A1 | 2/2008 | Massie et al. |

(56) References Cited

U.S. PATENT DOCUMENTS

| | | |
|---|---|---|
| 2008/0057461 A1 | 3/2008 | Cheng et al. |
| 2008/0057462 A1 | 3/2008 | Kitching et al. |
| 2008/0076086 A1 | 3/2008 | Kitching et al. |
| 2008/0085487 A1 | 4/2008 | Kuo et al. |
| 2008/0113314 A1 | 5/2008 | Pierson et al. |
| 2008/0115791 A1 | 5/2008 | Heine |
| 2008/0118882 A1 | 5/2008 | Su |
| 2008/0141534 A1 | 6/2008 | Hilliard |
| 2008/0182220 A1 | 7/2008 | Chishti et al. |
| 2008/0206702 A1 | 8/2008 | Hedge et al. |
| 2008/0215176 A1 | 9/2008 | Borovinskih et al. |
| 2008/0233528 A1 | 9/2008 | Kim et al. |
| 2008/0233530 A1 | 9/2008 | Cinader |
| 2008/0248438 A1 | 10/2008 | Desimone et al. |
| 2008/0248443 A1 | 10/2008 | Chisti et al. |
| 2008/0261165 A1 | 10/2008 | Steingart et al. |
| 2008/0268400 A1 | 10/2008 | Moss et al. |
| 2008/0280247 A1 | 11/2008 | Sachdeva et al. |
| 2008/0305451 A1 | 12/2008 | Kitching et al. |
| 2008/0305453 A1 | 12/2008 | Kitching et al. |
| 2009/0081604 A1 | 3/2009 | Fisher |
| 2009/0098502 A1 | 4/2009 | Andreiko |
| 2009/0117510 A1 | 5/2009 | Minium |
| 2009/0191502 A1 | 7/2009 | Cao et al. |
| 2009/0269714 A1 | 10/2009 | Knopp |
| 2009/0280450 A1 | 11/2009 | Kuo |
| 2009/0291407 A1* | 11/2009 | Kuo ............ A61C 1/084 433/24 |
| 2009/0291408 A1* | 11/2009 | Stone-Collonge ..... A61C 7/002 433/24 |
| 2010/0036682 A1 | 2/2010 | Trosien et al. |
| 2010/0055635 A1 | 3/2010 | Kakavand |
| 2010/0086890 A1 | 4/2010 | Kuo |
| 2010/0138025 A1 | 6/2010 | Morton et al. |
| 2010/0167225 A1 | 7/2010 | Kuo |
| 2010/0173266 A1 | 7/2010 | Lu et al. |
| 2010/0179789 A1 | 7/2010 | Sachdeva et al. |
| 2010/0239992 A1 | 9/2010 | Brandt et al. |
| 2010/0280798 A1 | 11/2010 | Pattijn et al. |
| 2011/0005527 A1 | 1/2011 | Andrew et al. |
| 2011/0015591 A1 | 1/2011 | Hanson et al. |
| 2011/0020761 A1 | 1/2011 | Kalili |
| 2011/0039223 A1 | 2/2011 | Li |
| 2011/0091832 A1 | 4/2011 | Kim et al. |
| 2011/0114100 A1 | 5/2011 | Alvarez et al. |
| 2011/0123944 A1 | 5/2011 | Knopp et al. |
| 2011/0129786 A1 | 6/2011 | Chun et al. |
| 2011/0159451 A1 | 6/2011 | Kuo et al. |
| 2011/0165533 A1 | 7/2011 | Li et al. |
| 2011/0269092 A1 | 11/2011 | Kuo et al. |
| 2011/0269097 A1 | 11/2011 | Sporbert et al. |
| 2011/0270588 A1 | 11/2011 | Kuo et al. |
| 2011/0281229 A1 | 11/2011 | Abolfathi |
| 2012/0028221 A1 | 2/2012 | Williams |
| 2012/0035901 A1 | 2/2012 | Kitching et al. |
| 2012/0123577 A1 | 5/2012 | Chapoulaud et al. |
| 2012/0150494 A1 | 6/2012 | Anderson et al. |
| 2012/0186589 A1 | 7/2012 | Singh |
| 2012/0199136 A1 | 8/2012 | Urbano |
| 2012/0214121 A1 | 8/2012 | Greenberg |
| 2012/0225399 A1 | 9/2012 | Teasdale |
| 2012/0225400 A1 | 9/2012 | Chishti et al. |
| 2012/0225401 A1 | 9/2012 | Kitching et al. |
| 2012/0227750 A1 | 9/2012 | Tucker |
| 2012/0244488 A1 | 9/2012 | Chishti et al. |
| 2012/0270173 A1 | 10/2012 | Pumphrey et al. |
| 2012/0288818 A1 | 11/2012 | Vendittelli |
| 2013/0004634 A1 | 1/2013 | McCaskey et al. |
| 2013/0022255 A1 | 1/2013 | Chen et al. |
| 2013/0052625 A1 | 2/2013 | Wagner |
| 2013/0078593 A1 | 3/2013 | Andreiko |
| 2013/0081271 A1 | 4/2013 | Farzin-Nia et al. |
| 2013/0085018 A1 | 4/2013 | Jensen et al. |
| 2013/0095446 A1 | 4/2013 | Andreiko et al. |
| 2013/0122445 A1 | 5/2013 | Marston |
| 2013/0122448 A1 | 5/2013 | Kitching |
| 2013/0157213 A1 | 6/2013 | Arruda |
| 2013/0201450 A1 | 8/2013 | Bailey et al. |
| 2013/0204583 A1 | 8/2013 | Matov et al. |
| 2013/0230819 A1 | 9/2013 | Arruda |
| 2013/0231899 A1 | 9/2013 | Khardekar et al. |
| 2013/0236848 A1 | 9/2013 | Arruda |
| 2013/0266906 A1 | 10/2013 | Soo |
| 2013/0302742 A1 | 11/2013 | Li et al. |
| 2013/0308846 A1 | 11/2013 | Chen et al. |
| 2013/0317800 A1 | 11/2013 | Wu et al. |
| 2013/0323665 A1 | 12/2013 | Dinh et al. |
| 2013/0325431 A1 | 12/2013 | See et al. |
| 2014/0023980 A1 | 1/2014 | Kitching et al. |
| 2014/0072926 A1 | 3/2014 | Valoir |
| 2014/0073212 A1 | 3/2014 | Lee |
| 2014/0076332 A1 | 3/2014 | Luco |
| 2014/0122027 A1 | 5/2014 | Andreiko et al. |
| 2014/0124968 A1 | 5/2014 | Kim |
| 2014/0167300 A1 | 6/2014 | Lee |
| 2014/0172375 A1 | 6/2014 | Grove |
| 2014/0178830 A1 | 6/2014 | Widu |
| 2014/0193765 A1 | 7/2014 | Kitching et al. |
| 2014/0193767 A1 | 7/2014 | Li et al. |
| 2014/0229878 A1* | 8/2014 | Wen ............ A61C 7/00 715/771 |
| 2014/0242532 A1 | 8/2014 | Arruda |
| 2014/0255864 A1 | 9/2014 | Machata et al. |
| 2014/0272757 A1 | 9/2014 | Chishti |
| 2014/0287376 A1 | 9/2014 | Hultgren et al. |
| 2014/0288894 A1 | 9/2014 | Chishti et al. |
| 2014/0315153 A1 | 10/2014 | Kitching |
| 2014/0315154 A1 | 10/2014 | Jung et al. |
| 2014/0067335 A1 | 11/2014 | Andreiko |
| 2014/0329194 A1 | 11/2014 | Sachdeva et al. |
| 2014/0349242 A1 | 11/2014 | Phan et al. |
| 2014/0358497 A1* | 12/2014 | Kuo ............ A61C 7/002 703/1 |
| 2014/0363779 A1 | 12/2014 | Kopelman |
| 2014/0370452 A1 | 12/2014 | Tseng |
| 2015/0004553 A1 | 1/2015 | Li et al. |
| 2015/0004554 A1 | 1/2015 | Cao et al. |
| 2015/0018956 A1 | 1/2015 | Steinmann et al. |
| 2015/0025907 A1 | 1/2015 | Trosien et al. |
| 2015/0044623 A1 | 2/2015 | Rundlett |
| 2015/0044627 A1 | 2/2015 | German |
| 2015/0057983 A1 | 2/2015 | See et al. |
| 2015/0064641 A1 | 3/2015 | Gardner |
| 2015/0093713 A1 | 4/2015 | Chen et al. |
| 2015/0093714 A1 | 4/2015 | Kopelman |
| 2015/0125802 A1 | 5/2015 | Tal |
| 2015/0128421 A1 | 5/2015 | Mason et al. |
| 2015/0157421 A1 | 6/2015 | Martz et al. |
| 2015/0182303 A1 | 7/2015 | Abraham et al. |
| 2015/0182321 A1 | 7/2015 | Karazivan et al. |
| 2015/0216626 A1 | 8/2015 | Ranjbar |
| 2015/0216627 A1 | 8/2015 | Kopelman |
| 2015/0238280 A1 | 8/2015 | Wu et al. |
| 2015/0238282 A1 | 8/2015 | Kuo et al. |
| 2015/0238283 A1 | 8/2015 | Tanugula et al. |
| 2015/0238284 A1 | 8/2015 | Wu et al. |
| 2015/0245887 A1 | 9/2015 | Izugami et al. |
| 2015/0254410 A1 | 9/2015 | Sterental et al. |
| 2015/0265376 A1 | 9/2015 | Kopelman |
| 2015/0289949 A1 | 10/2015 | Moss et al. |
| 2015/0289950 A1 | 10/2015 | Khan |
| 2015/0305830 A1 | 10/2015 | Howard et al. |
| 2015/0305831 A1 | 10/2015 | Cosse |
| 2015/0305919 A1 | 10/2015 | Stubbs et al. |
| 2015/0313687 A1 | 11/2015 | Blees et al. |
| 2015/0320518 A1 | 11/2015 | Namiranian et al. |
| 2015/0320532 A1 | 11/2015 | Matty et al. |
| 2015/0335399 A1 | 11/2015 | Caraballo |
| 2015/0335404 A1 | 11/2015 | Webber et al. |
| 2015/0336299 A1 | 11/2015 | Tanugula et al. |
| 2015/0342464 A1 | 12/2015 | Wundrak et al. |
| 2015/0351870 A1* | 12/2015 | Mah ............ G16H 10/60 600/408 |
| 2015/0351871 A1 | 12/2015 | Chishti et al. |

(56) References Cited

U.S. PATENT DOCUMENTS

| | | |
|---|---|---|
| 2015/0359609 A1 | 12/2015 | Khan |
| 2015/0366637 A1 | 12/2015 | Kopelman et al. |
| 2015/0366638 A1 | 12/2015 | Kopelman et al. |
| 2016/0000527 A1 | 1/2016 | Arruda |
| 2016/0008095 A1 | 1/2016 | Matov et al. |
| 2016/0008097 A1 | 1/2016 | Chen et al. |
| 2016/0051341 A1 | 2/2016 | Webber |
| 2016/0051342 A1 | 2/2016 | Phan et al. |
| 2016/0051348 A1 | 2/2016 | Boerjes et al. |
| 2016/0067013 A1 | 3/2016 | Morton et al. |
| 2016/0067014 A1 | 3/2016 | Kottemann et al. |
| 2016/0074137 A1 | 3/2016 | Kuo et al. |
| 2016/0074138 A1 | 3/2016 | Kitching et al. |
| 2016/0095668 A1 | 4/2016 | Kuo et al. |
| 2016/0095670 A1 | 4/2016 | Witte et al. |
| 2016/0106521 A1 | 4/2016 | Tanugula et al. |
| 2016/0120617 A1 | 5/2016 | Lee |
| 2016/0120621 A1 | 5/2016 | Li et al. |
| 2016/0128803 A1 | 5/2016 | Webber et al. |
| 2016/0135924 A1 | 5/2016 | Choi et al. |
| 2016/0135925 A1 | 5/2016 | Mason et al. |
| 2016/0135926 A1 | 5/2016 | Djamchidi |
| 2016/0135927 A1 | 5/2016 | Boltunov et al. |
| 2016/0157961 A1 | 6/2016 | Lee |
| 2016/0166363 A1* | 6/2016 | Varsano ............... A61C 13/34 703/1 |
| 2016/0175068 A1 | 6/2016 | Cai et al. |
| 2016/0175069 A1 | 6/2016 | Korytov et al. |
| 2016/0184129 A1 | 6/2016 | Liptak et al. |
| 2016/0193014 A1 | 7/2016 | Morton et al. |
| 2016/0199216 A1 | 7/2016 | Cam et al. |
| 2016/0203604 A1 | 7/2016 | Gupta et al. |
| 2016/0206402 A1 | 7/2016 | Kitching et al. |
| 2016/0220200 A1 | 8/2016 | Sanholm et al. |
| 2016/0228213 A1* | 8/2016 | Tod ....................... G16H 10/20 |
| 2016/0256240 A1 | 9/2016 | Shivapuja et al. |
| 2016/0310235 A1* | 10/2016 | Derakhshan ........... A61C 7/002 |
| 2016/0338799 A1 | 11/2016 | Wu et al. |
| 2016/0367339 A1 | 12/2016 | Khardekar et al. |
| 2017/0007359 A1 | 1/2017 | Kopelman et al. |
| 2017/0065373 A1 | 3/2017 | Martz et al. |
| 2017/0079748 A1 | 3/2017 | Andreiko |
| 2017/0100207 A1 | 4/2017 | Wen |
| 2017/0100208 A1 | 4/2017 | Wen |
| 2017/0100209 A1 | 4/2017 | Wen |
| 2017/0100210 A1 | 4/2017 | Wen |
| 2017/0100211 A1 | 4/2017 | Wen |
| 2017/0100214 A1 | 4/2017 | Wen |
| 2017/0224444 A1 | 8/2017 | Viecilli et al. |
| 2017/0231721 A1 | 8/2017 | Akeel et al. |
| 2017/0325911 A1 | 11/2017 | Marshall |
| 2018/0014912 A1 | 1/2018 | Radmand |
| 2018/0028065 A1 | 2/2018 | Elbaz et al. |
| 2018/0042708 A1 | 2/2018 | Caron et al. |
| 2018/0055611 A1 | 3/2018 | Sun et al. |
| 2018/0078343 A1 | 3/2018 | Falkel |
| 2018/0078344 A1 | 3/2018 | Falkel |
| 2018/0078347 A1 | 3/2018 | Falkel |
| 2018/0092714 A1 | 4/2018 | Kitching et al. |
| 2018/0092715 A1 | 4/2018 | Kitching et al. |
| 2018/0125610 A1 | 5/2018 | Carrier, Jr. et al. |
| 2018/0158544 A1 | 6/2018 | Trosien et al. |
| 2018/0161126 A1 | 6/2018 | Marshall et al. |
| 2018/0168781 A1 | 6/2018 | Kopelman et al. |
| 2018/0174367 A1 | 6/2018 | Marom et al. |
| 2018/0333226 A1 | 11/2018 | Tsai et al. |
| 2018/0344431 A1 | 12/2018 | Kuo et al. |
| 2019/0008612 A1 | 1/2019 | Kitching et al. |
| 2019/0046297 A1 | 2/2019 | Kopelman et al. |
| 2019/0090987 A1 | 3/2019 | Hung |
| 2019/0155789 A1 | 5/2019 | Dorman |
| 2019/0231478 A1* | 8/2019 | Kopelman ............. A61C 7/002 |
| 2019/0321135 A1 | 10/2019 | Wen |
| 2019/0343602 A1 | 11/2019 | Wen |
| 2019/0350680 A1 | 11/2019 | Chekh et al. |
| 2019/0358002 A1 | 11/2019 | Falkel |
| 2019/0388189 A1 | 12/2019 | Shivapuja et al. |
| 2020/0000552 A1 | 1/2020 | Mednikov et al. |
| 2020/0047868 A1 | 2/2020 | Young et al. |
| 2020/0081413 A1 | 3/2020 | Georg et al. |
| 2020/0105028 A1 | 4/2020 | Gao et al. |
| 2020/0146775 A1 | 5/2020 | Wen |
| 2020/0170762 A1 | 6/2020 | Falkel |
| 2020/0205936 A1 | 7/2020 | Wen |
| 2020/0214598 A1 | 7/2020 | Li et al. |
| 2020/0214801 A1 | 7/2020 | Wang et al. |
| 2020/0253693 A1 | 8/2020 | Wen |
| 2020/0316856 A1 | 10/2020 | Mojdeh et al. |
| 2020/0345459 A1 | 11/2020 | Schueller et al. |
| 2020/0357186 A1 | 11/2020 | Pokotilov et al. |
| 2020/0360120 A1 | 11/2020 | Inoue et al. |
| 2020/0390523 A1 | 12/2020 | Sato et al. |
| 2021/0106404 A1 | 4/2021 | Wen |
| 2021/0153981 A1 | 5/2021 | Falkel |
| 2021/0186668 A1 | 6/2021 | Falkel |
| 2021/0244518 A1 | 8/2021 | Ryu et al. |
| 2021/0282899 A1 | 9/2021 | Wen |
| 2021/0369417 A1 | 12/2021 | Wen et al. |
| 2021/0393376 A1 | 12/2021 | Wu et al. |
| 2021/0393385 A1 | 12/2021 | Parkar et al. |
| 2022/0054232 A1 | 2/2022 | Wen et al. |
| 2022/0265395 A1 | 8/2022 | Falkel |
| 2022/0266577 A1 | 8/2022 | Sharma et al. |
| 2022/0323182 A1 | 10/2022 | Lee |
| 2022/0409338 A1 | 12/2022 | Cao et al. |
| 2023/0005593 A1 | 1/2023 | Raslambekov |
| 2023/0053766 A1 | 2/2023 | Cao et al. |
| 2023/0058890 A1 | 2/2023 | Kenworthy |
| 2023/0233288 A1 | 7/2023 | Wen |
| 2023/0240808 A1 | 8/2023 | Schueller et al. |
| 2023/0320565 A1 | 10/2023 | Falkel |
| 2023/0380936 A1 | 11/2023 | Wen |
| 2023/0380938 A1 | 11/2023 | Sharma et al. |
| 2023/0380939 A1 | 11/2023 | Lai et al. |
| 2023/0414324 A1 | 12/2023 | Wen |
| 2024/0299134 A1 | 9/2024 | Wen |

FOREIGN PATENT DOCUMENTS

| | | |
|---|---|---|
| CN | 1997324 | 7/2007 |
| CN | 101427256 | 5/2009 |
| CN | 101636122 | 1/2010 |
| CN | 102438545 | 5/2012 |
| CN | 105748163 | 7/2016 |
| CN | 106580509 | 4/2017 |
| EP | 1474062 | 4/2011 |
| EP | 2056734 | 9/2015 |
| EP | 2957252 | 12/2015 |
| HK | 40004866 B | 8/2022 |
| JP | 2010-528748 | 8/2010 |
| JP | 2013-081785 | 5/2013 |
| JP | 2019-013463 | 1/2019 |
| JP | 2019-529042 | 10/2019 |
| JP | 2019-537033 | 12/2019 |
| KR | 2004-46323 | 10/2009 |
| WO | WO 2001/082192 | 11/2001 |
| WO | WO 2002/047571 | 6/2002 |
| WO | WO 2003/063721 | 8/2003 |
| WO | WO 2004/028391 | 4/2004 |
| WO | WO 2005/086058 | 9/2005 |
| WO | WO 2004/098379 | 11/2005 |
| WO | WO 2006/050452 | 5/2006 |
| WO | WO 2006/096558 | 9/2006 |
| WO | WO 2008/026064 | 3/2008 |
| WO | WO 2008/102132 | 8/2008 |
| WO | WO 2008/118546 | 10/2008 |
| WO | WO 2008/149222 | 12/2008 |
| WO | WO 2009/057937 | 5/2009 |
| WO | WO 2009/068892 | 6/2009 |
| WO | WO 2016/100577 | 6/2016 |
| WO | WO 2016/004415 | 7/2016 |
| WO | WO 2017/062207 | 4/2017 |
| WO | WO 2017/062208 | 4/2017 |
| WO | WO 2017/062209 | 4/2017 |

(56) References Cited

FOREIGN PATENT DOCUMENTS

| | | |
|---|---|---|
| WO | WO 2017/062210 | 4/2017 |
| WO | WO 2018/057622 | 3/2018 |
| WO | WO 2018/112273 | 6/2018 |
| WO | WO 2018/118200 | 6/2018 |
| WO | WO 2020/222905 | 11/2020 |
| WO | WO 2020/223384 | 11/2020 |
| WO | WO 2020/239429 | 12/2020 |
| WO | WO 2020/257724 | 12/2020 |
| WO | WO 2021/105878 | 6/2021 |
| WO | WO 2021/247145 | 12/2021 |
| WO | WO 2021/247950 | 12/2021 |
| WO | WO 2022/040671 | 2/2022 |
| WO | WO 2022/178514 | 8/2022 |
| WO | WO 2023/023417 | 2/2023 |
| WO | WO 2023/023418 | 2/2023 |
| WO | WO 2023/230460 | 11/2023 |

\* cited by examiner

COMBINED ORTHODONTIC MOVEMENT OF TEETH WITH COSMETIC RESTORATION

CROSS-REFERENCE TO RELATED APPLICATIONS

This application claims priority to U.S. Provisional Application No. 62/397,783 filed Sep. 21, 2016, which is herein incorporated by reference in its entirety for all purposes.

BACKGROUND

1. Technical Field

This disclosure relates generally to cosmetic dentistry and orthodontic care. More specifically, this disclosure relates to systems and methods that can electronically simulate treatment strategies involving cosmetic dental restorations with and without preparatory orthodontic treatment.

2. Background of the Art

Cosmetic dentistry and the orthodontic movement of teeth can each be used to improve the smiles of patients. Cosmetic dentistry involves reshaping or sculpting the teeth and orthodontics involves moving the teeth.

Cosmetic dentistry is currently practiced separately from orthodontics such that the two treatments are either implemented alone or are otherwise not coordinated with one another. Patients are also often unaware that they have a choice between the two treatments, being instead guided by whoever they consult with first—the dentist or the orthodontist.

Compared to orthodontics, cosmetic dentistry gives patients the ability to improve their smiles in less time, but often at the high cost of losing valuable tooth structure to accommodate the corresponding cosmetic restoration.

A need therefore currently exists not only to educate patients as to their treatment options, but also to lessening the extent of tooth loss associated with cosmetic dentistry and/or to reducing the amount of time required to effect the orthodontic movement of teeth to achieve smiles that patients are ultimately happy with.

Previous efforts to improve this field have more narrowly focused on improvements to cosmetic dentistry alone or to improvements to the orthodontic movement of teeth alone. The two modalities have not yet been coordinated with one another or otherwise combined. However, combining orthodontic and cosmetic dentistry can be a valuable alternative to either treatment alone.

The present disclosure addresses this need and adds this value by utilizing digitally gathered information to educate patients on their different treatment options, including cosmetic dentistry alone, orthodontics alone, and the option of pretreating the teeth with orthodontic movement prior to cosmetic restoration. The present disclosure also adds value by being able to simulate each option.

A need also currently exists to lessen the amount of tooth loss associated with cosmetic dentistry. The present disclosure addresses this by orthodontically repositioning the teeth into an arrangement that lessens the amount of reshaping or sculpting required for the corresponding cosmetic dentistry restorations.

Comprehensive cosmetic dental treatments should include all alternatives in considering the best options for any given patient, including alternatives which involve the orthodontic movement of teeth. While there are currently programs that can give dentists and patients orthodontic models or cosmetic mock ups with stone models and wax ups, there is currently no digital program that can coordinate the orthodontic movement of teeth in preparation for a cosmetic restoration.

BRIEF SUMMARY OF THE INVENTION

This disclosure relates generally to cosmetic and orthodontic dental treatments.

More specifically, systems and methods are disclosed that can electronically simulate treatment strategies involving cosmetic dental restorations with and without preparatory orthodontic treatment.

Methods of coordinating orthodontic and cosmetic dental treatments are disclosed. For example, a method is disclosed that can include determining an orthodontic treatment plan to at least partially correct for a malocclusion of at least one tooth. The method can include determining an amount of cosmetic restoration of the at least one tooth based on a degree of partial correction of the malocclusion. The method can include preparing the at least one tooth for the cosmetic restoration by orthodontically moving the tooth from a first position to a second position. The method can include cosmetically restoring the at least one tooth when the at least one tooth is in the second position.

Methods of coordinating orthodontic and cosmetic dental treatments are disclosed. For example, a method is disclosed that can include simulating an orthodontic treatment alone. The method can include simulating a cosmetic dental treatment alone. The method can include simulating sequentially pre-treating the teeth with the orthodontic treatment before beginning the cosmetic dental treatment. The method can include automatically or manually selecting a simulated treatment plan. The method can include orthodontically moving teeth from a teeth first position to a teeth second position. The method can include designing a cosmetic restoration based on the teeth second position.

BRIEF DESCRIPTION OF THE DRAWINGS

The drawings shown and described are exemplary embodiments and non-limiting. Like reference numerals indicate identical or functionally equivalent features throughout.

DETAILED DESCRIPTION

Systems and methods are disclosed that can electronically evaluate the dentition, simulate various cosmetic and/or orthodontic treatment options, and optionally produce orthodontic trays that can affect the orthodontic treatment options selected. The systems and methods disclosed can simulate treatment with cosmetic dentistry alone, with orthodontic treatment alone, and/or with a coordinated combination of treatment in which a preparatory orthodontic treatment is applied before the cosmetic restoration is carried out. The systems and methods disclosed can involve executing a computer algorithm that can model these various treatment options.

System—Overview

Figure 1:
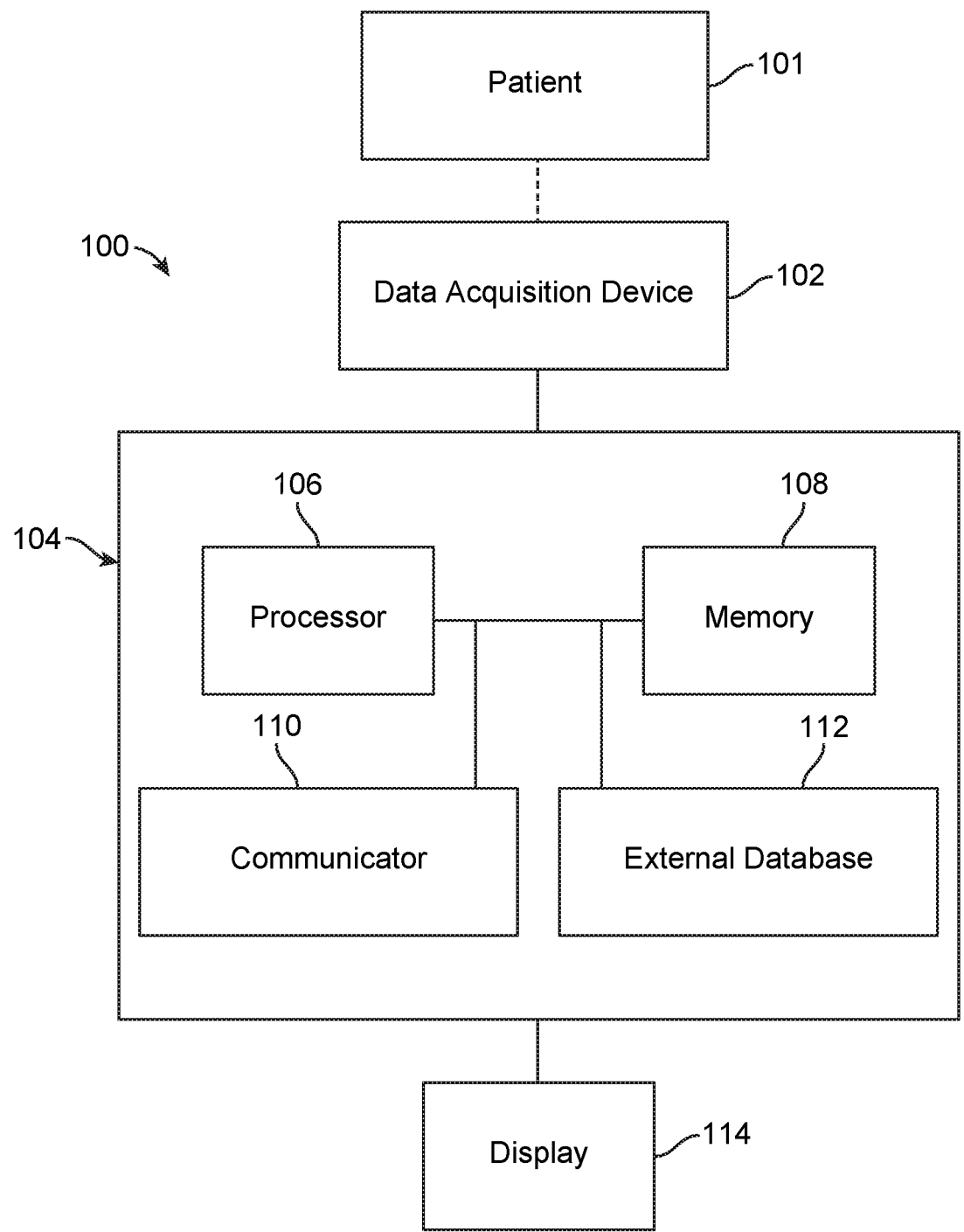
FIG. 1 illustrates a schematic of a variation of an electronic dental examination and documentation system.

FIG. 1 illustrates a schematic of a variation of an electronic dental examination system 100. The system 100 can have a data acquisition device 102 and an examination unit 104. The data acquisition device 102 can be in wired or wireless communication with the examination unit 104. The examination unit 104 can receive data from one or more data acquisition devices 102, for example, separately, sequentially, and/or simultaneously. The data acquisition device 102 can be used to capture or image (e.g., scan, photograph, x-ray) the dentition. FIG. 1 illustrates that the data acquisition device 102 can acquire one or more teeth of a patient 101, for example, by electronically capturing or imaging the dentition. The acquiring is indicated by the dotted line that extends between the patient 101 and the data acquisition device 102. The dotted line also represents wired or wireless data transfer to and/or from the data acquisition device 102 and the examination unit 104.

The data acquisition device 102 can be used to create a digital impression of the dentition, for example, the entire dentition, a subset thereof, a single tooth, one or more portions of multiple teeth, a portion of a single tooth, or any combination thereof. In this way, the data acquisition device 102 can be used to digitally record a person's teeth in preparation for orthodontic and/or cosmetic dental treatment.

The data acquisition device 102 can be a scanner, an x-ray device, a camera, or any combination thereof. For example, the data acquisition device 102 can be a handheld scanner, radiographic imaging device, camera, or any combination thereof, for example, a handheld intraoral scanner.

The examination unit 104 can process data received and/or retrieved from the data acquisition device 102. The examination unit 104 can be local or remote relative to the data acquisition device 102. For example, the examination unit 104 can be on or be part of a server such as a cloud server, a cluster server, and/or a storage server. The examination unit 104 can analyze data from one or multiple data acquisition devices 102 and can be configured to store raw data (e.g., unprocessed data, unanalyzed data), processed data, data derived from raw and/or processed data, or any combination thereof, for example, on a server or on a local memory medium.

FIG. 1 further illustrates that the examination unit 104 can have one or multiple processing units 106, memory units 108, communication units 110, external databases 112, or any combination thereof. The processing unit 106 can be coupled to the memory and communication units 108, 110 through high-speed buses.

The processing unit 106 can include one or more central processing units (CPUs), graphical processing units (GPUs), application-specific integrated circuits (ASICs), field-programmable gate arrays (FPGAs), or any combination thereof. The processing unit 106 can be programmable processor. The processing unit 106 can execute software stored in the memory unit 108 to execute the methods, instructions, and/or algorithms described herein. The processing unit 106 can be an embedded processor, a processor core, a microprocessor, a logic circuit, a hardware finite state machine (FSM), a digital signal processor (DSP), or any combination thereof. As a more specific example, the processing unit 104 can be a 32-bit or a 64-bit processor.

The memory unit 108 can store software, data, logs, or any combination thereof. The data stored can be raw data, processed data, data derived from raw and/or processed data, or any combination thereof. For example, the memory unit 108 can store data received from the data acquisition device 102, as well as the output from the processing unit 106 after the data acquisition device 102 data has been analyzed and/or modeled. The memory unit 108 can be an internal memory of the examination unit 104 as shown in FIG. 1, or it can be an external memory, such as a memory residing on a storage node, a cloud server, and/or a storage server. The memory unit 108 can be a volatile memory or a non-volatile memory. For example, the memory unit 108 can be a non-volatile storage medium such as non-volatile random access memory (NVRAM), flash memory, disk storage, or a volatile storage such as static random access memory (SRAM). The memory unit 108 can be the main storage unit for the examination unit 104.

The communication unit 110 can include one or more wired or wireless communication interfaces. For example, the communication unit 110 can be a network interface card of the examination unit 104. The communication unit 110 can be a wireless modem or a wired modem, for example, a WiFi modem, a 3G modem, a 4G modem, an LTE modem. Alternatively, or in combination, the communication unit 110 can be a Bluetooth™ component, a radio receiver, an antenna, or any combination thereof. For example, the communication unit 110 can be a server communication unit. The examination unit 104 can transmit and/or receive data packets and/or messages using the communication unit 110. The communication unit 110 can connect to or communicatively couple with one or more wireless signal transceivers and/or networks.

The examination unit 104 can include an external database 112 separate from, alternative to, and/or additional to the memory 108. The memory 108 and/or the database 112 can be internal and/or external to the examination unit 104, and can each be non-volatile and/or volatile memory. Alternatively, or in combination, the database 112 can be integrated or otherwise combined with the memory 108. The external database 112 can be on or be part of a server, for example, a cloud server, and/or a storage server.

The memory 108 and/or the external database 112 can be configured to store patient-specific data and/or non-patient specific data. For example, the memory 108 can store patient-specific data and the external database 112 can store non-patient specific data recorded from one or more patients different from patient 101.

FIG. 1 also illustrates that the system 100 can have one or more displays 114. The display 114 can display data acquisition results and/or the analyses thereof. The display 114 can be integrated with the device or system having the examination unit 104 and/or can be part of a standalone device in wired or wireless communication with the examination unit 104. For example, the display 114 can be part of a computer, a smartphone, a tablet, a laptop, a smartwatch, or any combination thereof. The device having the display 114 can be in communication with the data acquisition device 102, one or more other devices, the cloud, and/or one or more networks.

Alternatively, or in combination, the examination unit 104 can be part of or integrated with the device or system having the display 114, including a personal or portable device, for example, a computer, a smartphone, a tablet, a laptop, a smartwatch, or any combination thereof. Executable code can be installed on memory (e.g., memory 108) of the device having the display 114. When the executable code is executed by the device, the device can perform the instructions, processes, methods, and operations disclosed and contemplated herein, such that the device can analyze data acquisition results and model orthodontic and/or cosmetic dental restoration treatment options. For example, a smartphone application can be downloaded onto a smartphone that has executable code configured to carry out the various functions of the examination unit 104. Alternatively, or in combination, executable code can be located on the cloud, for example, on a server. The device (e.g., a smartphone) can query the server to run the executable code on the server to carry out the instructions, processes, methods, and operations disclosed and contemplated herein.

Alternatively, or in combination, the examination unit 104 can comprise downloadable executable code that utilizes existing processing, memory, and data storage features of a device and/or the cloud.

System—Dentition Evaluation

Figure 2A:
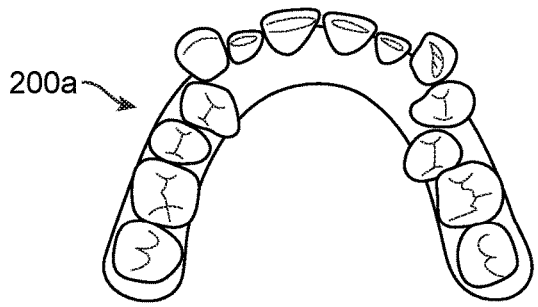
FIG. 2A illustrates a diagrammatic representation of a variation of an occlusal view of teeth having a crowded dentition.
Figure 2B:
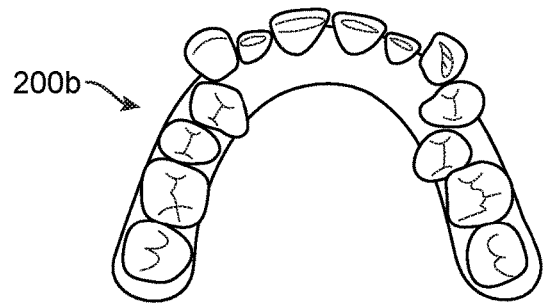
FIG. 2B illustrates a diagrammatic representation of a variation of a digital impression of the teeth of FIG. 2A.

FIG. 2A illustrates a schematic of a variation of an occlusal view of teeth 200a having a crowded arrangement. A system (e.g., system 100) can be used to create a digital impression of the teeth 200a. For example, FIG. 2B illustrates a schematic variation of a digital impression 200b of the teeth 200a. Although the digital impression 200b is shown in the same occlusal view as the teeth 200a of FIG. 2A, any two-dimensional or three-dimensional view is appreciated. The teeth (e.g., teeth 200a) and the corresponding digital impression (e.g., impression 200b) can include the maxillary and/or mandibular dentition, or a portion thereof. For example, FIGS. 2A and 2B illustrate that the teeth 200a and the corresponding digital impression 200b can be a maxillary dentition.

The system (e.g., system 100) can evaluate a digitally acquired dentition to determine the arrangement of the teeth (e.g., teeth 200a), including the presence and extent of any malocclusions, for example, by determining the bounds and relative positions of the teeth. The system 100 can determine the cosmetic and/or orthodontic needs of a patient, and/or the system 100 can receive input from a user (e.g., dentist, orthodontist) regarding the cosmetic and/or orthodontic needs of a patient. For example, the system 100 can identify one or more candidate teeth for cosmetic dental restoration as well as one or more candidate teeth for orthodontic repositioning. Based on these determinations, the examination unit 104 can make orthodontic and/or cosmetic dental restoration treatment recommendations, as well as design treatment plans (e.g., orthodontic treatment alone, or cosmetic dental treatment with or without one or more preparatory orthodontic treatments). The recommendations can involve repositioning and/or restoring one or more teeth, including, for example the candidate teeth identified for orthodontic repositioning and/or the candidate teeth identified for cosmetic restoration.

The system 100 can determine orthodontic needs alone and/or can determine orthodontic preparation needs when the orthodontic treatment is coordinated with subsequent cosmetic restoration. For example, the system 100 (e.g., the examination unit 104) can identify the teeth in need of or that could benefit from cosmetic restoration and/or orthodontic movement. The system 100 can pretreat the teeth 100a with orthodontic movement to better position them for cosmetic reshaping and sculpting. This can involve moving one or multiple teeth to a better position for the placement of cosmetic dental restorations. Such orthodontic pretreatment prior to the reshaping of the teeth and placement of the cosmetic restorations can desirably reduce the amount of tooth structure destruction that would otherwise be necessary if the teeth were not first pretreated with orthodontic movement. Orthodontic pretreatment is also referred to as orthodontic preparatory treatment, as the orthodontic movement of teeth is done to accommodate the placement of cosmetic restorations. A patient's orthodontic preparation needs can correspond to one or more preparatory orthodontic treatments configured to be applied before the cosmetic restoration is applied. Orthodontic positioning can also be evaluated for cosmetic restorations that do not need any preparation at all, known as prep-less veneers.

The cosmetic dental restorations can include, for example, bonding, veneers (e.g., porcelain veneers, composite veneers, prep-less veneers), crowns, or any combination thereof. The system 100 can determine the restoration thicknesses for one or multiple cosmetic treatments. For example, the system 100 can determine the restoration thicknesses with and/or without pretreating the teeth with orthodontic movement. The restoration thicknesses recommended by the system 100 can depend on the extent of orthodontic pretreatment recommended, as well as on the type of cosmetic restoration used (e.g., veneer and/or cap).

The system 100 can analyze the data associated with the data acquisition of the acquired teeth 200a (e.g., the digital impression 200b) to coordinate the orthodontic repositioning of one or more teeth prior to the placement of one or multiple cosmetic dental restorations.

System—Treatment Simulation

The system 100 can electronically model the different treatment options, including the orthodontic movement of teeth alone, cosmetic restorations alone, and/or the coordinated combined treatment of sequentially first pretreating the teeth with orthodontic movement, subsequently preparing the teeth for cosmetic restoration (e.g., via reshaping, sculpting), and then placing the cosmetic restorations on the teeth (e.g., teeth 200a). The system 100 can simulate each of the treatment options, for example, for each type of cosmetic restoration treatment product (e.g., bonding, veneer, and/or crown).

The different treatment options can be simulated on the digital impression 200b. The orthodontic progression and/or the end tooth positions can be simulated with and/or without the simulation of cosmetic dentistry. The simulated end tooth positions for orthodontic treatments in preparation for cosmetic restoration treatments can be the same as or different from the simulated end tooth positions for orthodontic treatments that do not have subsequent restoration treatments.

Figure 3A:
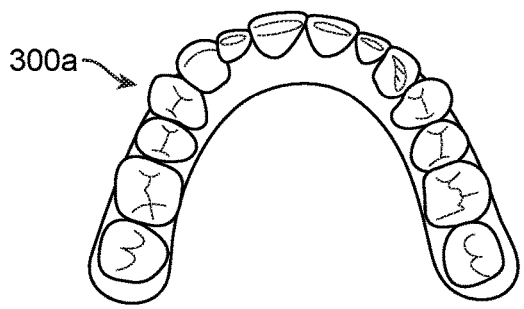
FIG. 3A illustrates a diagrammatic representation of a variation of an occlusal view of the teeth of FIG. 2A with an orthodontic correction ready for minimally invasive cosmetic dentistry.
Figure 3B:
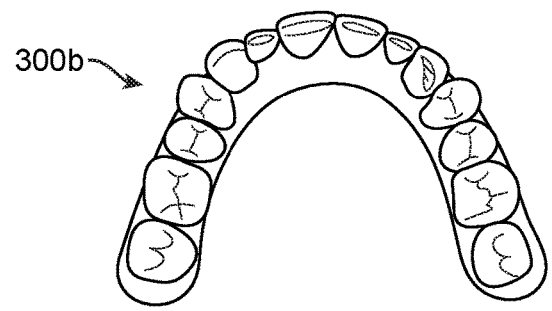
FIG. 3B illustrates a diagrammatic representation of a variation of a digital simulation of a final tooth arrangement of the teeth of FIG. 2A after an orthodontic preparatory treatment is applied to the teeth.

For example, FIG. 3A illustrates that the teeth 200a can be orthodontically repositioned into a new arrangement 300a in preparation for restorative cosmetic treatment. The new teeth arrangement 300a can be ready for minimally invasive cosmetic dentistry. FIG. 3B illustrates a schematic variation of a digital mockup 300b of the teeth 200a of FIG. 2A having a new arrangement due to orthodontic preparatory treatment. The digital mockup 300b can be the same or different as the resultant new arrangement 300a. FIG. 3B illustrates that the simulated arrangement 300b can be the same as the resultant new arrangement 300a.

Figure 4:
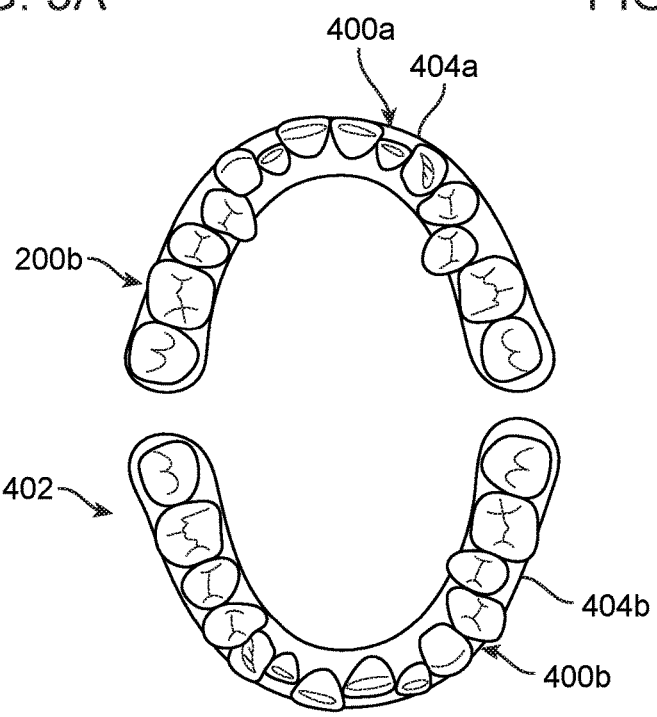
FIG. 4 illustrates a diagrammatic representation of a variation of an occlusal view of the digital impression of FIG. 2B with a simulated cosmetic dentistry treatment.

The system 100 can also model the restoration thickness and extent of preparation of the teeth 200a (e.g., orthodontic and/or cosmetic preparation) to obtain a desired cosmetic result, for example, on the digital impression 200b. The system 100 can create digital models of the teeth (also referred to as digital impressions), and an algorithm can then be used to create a cosmetic restoration model for each of the cosmetic restorations determined by the system 100 to be potentially useful. Parameters such as the thickness of the restorative material and the extent of the tooth removal can be modeled so that the possible results can be visualized. For example, FIG. 4 illustrates a schematic of a variation of a simulated cosmetic dentistry treatment 400a on the maxillary digital impression 200b of FIG. 2B in addition to a simulated cosmetic dentistry treatment 400b on the corresponding mandibular digital impression 402, for example, before or without the simulation of the orthodontic treatment 300b simulated in FIG. 3B. The maxillary and mandibular lines 404a, 404b can represent the facial aspect of planned restorative treatment (e.g., veneers), including both the thickness and the amount of tooth structure necessary to remove to give adequate thickness to the restorative treatment (e.g., veneers).

The models/simulations can desirably help patients make decisions on treatment protocols and outcomes. For example, the system 100 can have a computer algorithm configured to simulate the orthodontic movement that will allow for minimally invasive preparations of the teeth 200a as compared to treating with cosmetic restorations without first pre-treating the teeth 200a with orthodontics. Alternatively or additionally, the system 100 can combine the therapeutic orthodontic movement of teeth as well as digital mockup of the cosmetic restorative needs that can be converted to placeable or provisional restorations. The cosmetic restorations can be made of bonded ceramic or direct restorative material.

The models and simulations can be displayed on a display (e.g., display 114).

The models and simulations can give the dentist and patient the ability to evaluate orthodontic treatment alone, cosmetic dentistry alone or the combination of the two. Knowledge of the procedure through visualization will give patients and dentists alike the ability to make more informed decisions on their care. Many patients would like the quick fix of restorative cosmetic dentistry but do not understand the amount of tooth structure destruction that can be necessary for these procedures due to the tooth positions (e.g., relative positions, tooth rotations). The models and simulations can advantageously help patients understand the extent this destruction, both with and without being first pretreated with the orthodontic movement of one or more teeth.

To reiterate, the system 100 can create treatment protocols involving dental restorations alone, orthodontic treatments alone, or both, for example by using statistical analysis and simulating or otherwise modeling one or more treatment options.

This information can be transferred to a three-dimensional printed model or a direct printed tray, which can be used for a mockup of the restorations in the mouth. Alternatively or additionally, orthodontic software can position the teeth for a final result without any cosmetic dentistry for evaluation. A combination of the two can be evaluated as well.

The system 100 can produce digital and/or physical simulations/models.

System—Orthodontic Trays

The system 100 can be configured to design orthodontic trays (also referred to as aligners) for orthodontic preparatory treatment which is a precursor to cosmetic restoration. Additionally or alternatively, the system 100 can design standalone orthodontic trays unaffiliated with cosmetic restoration.

A series of oral trays can be designed to progressively reposition the maxillary and/or mandibular teeth in two or more successive steps, for example, as disclosed in WO 2016/004415, which is herein incorporated by reference in its entirety and for any purpose. Each oral tray in a series can have a tooth surface that has a geometry that corresponds to an intermediate or end tooth arrangement intended for the oral tray in the series. The oral trays can be sufficiently resilient to accommodate or conform to misaligned teeth, but apply sufficient force against the misaligned teeth to reposition the teeth to the intermediate or end arrangement as desired for the particular treatment step. A series of oral trays can have geometries selected to progressively reposition teeth from a first arrangement through one or more successive intermediate arrangements to a final arrangement. The final arrangement can correspond to the final orthodontic pretreatment position for one or more of a patient's teeth (e.g., teeth 200a), for example the entire dentition.

A series of trays can have 1 to 100 trays maxillary trays and 1 to 100 mandibular trays, for example, 1 to 55 maxillary trays and 1 to 55 mandibular trays, 1 to 50 maxillary trays and 1 to 50 mandibular trays, 1 to 45 maxillary trays and 1 to 45 mandibular trays, 1 to 40 maxillary trays and 1 to 40 mandibular trays, less than 40 maxillary trays 12 and less than 40 mandibular trays, or combinations thereof. For example, a series of trays can have 40, 41, 42, 43, 44, 45, 46, 47, 48, 49, or 50 maxillary trays and 40, 41, 42, 43, 44, 45, 46, 47, 48, 49, or 50 mandibular trays. The number of maxillary trays can be the same or different as the number mandibular trays in a series.

A single oral tray and/or a series of oral trays can be the orthodontic preparatory treatment that the system 100 designs in advance of cosmetic restoration.

The trays can orthodontically move the teeth into one or more correct physiological positions. The trays can orthodontically move the teeth into one or more positions that physiologically allows for less destructive cosmetic dental treatment, for example, into positions that allow for less reshaping and sculpting prior to placement of a cosmetic dental restoration. The first tray and/or any tray between the first and last trays can be configured to partially correct a malocclusion of at least one tooth by repositioning the at least one tooth into an intermediate position. The intermediate tooth arrangement that the first tray and/or any tray between the first and last trays are configured to reposition the teeth into can be a partial correction of a malocclusion of at least one tooth. The first tray and/or any tray between the first and last trays can each partially correct a malocclusion of at least one tooth by progressively moving the at least one tooth toward intermediate positions that are progressively more conducive to dental restoration, for example, because less of the at least one tooth will be destroyed, lost, sculpted, or reshaped in the intermediate positions relative to its previous position(s). The last tray can be configured to partially correct a malocclusion of at least one tooth by repositioning the at least one tooth into a restoration position (e.g., an end position). The restoration position can be an optimum position for the at least one tooth for dental restoration for a given treatment period (e.g., from about 1 month to about 12 or more months, including every 1 month increment within this range), for example, because less of the at least one tooth will be destroyed, lost, sculpted, or reshaped in the restoration position relative to its previous position(s). The restoration position can be a partial or complete correction of a malocclusion of the at least one tooth. The end tooth arrangement of the last tray can be a partial correction of a malocclusion of at least one tooth. The end tooth arrangement of the last tray can be a complete correction of a malocclusion of at least one tooth. The amount of cosmetic restoration of the at least one tooth can be based on the degree of partial correction of the malocclusion. The degree of partial correction can correspond to a percentage correction, for example, from about 1% correction to about 99% correction, including every 1% increment within this range, for example, 20%, 40%, 50%, 70%, and where 100% can correspond to complete correction of the malocclusion. A higher percentage correction can correspond to the same percentage decrease or a proportionate percentage decrease (e.g., 1:1, 1:2, 1:3, 1:4, 1:5) of the amount of reshaping or sculpting (e.g., destruction) of the at least one tooth that is required prior to placement of a dental restoration.

The intermediate and end tooth positions of the trays can be selected or otherwise coordinated with the sculpting and reshaping needs of cosmetic dental restoration. The intermediate and end tooth position of the "restoration" trays disclosed herein can be different than the intermediate and end tooth positions of orthodontic trays that are not configured to move teeth in preparation for dental restorations. The restoration trays disclosed herein can be designed to translate and/or rotate teeth along different paths, arcs, and/or angles relative to regular orthodontic aligner trays that are not moving teeth in preparation for a dental restoration. The system can simulate the progressive orthodontic movement teeth for the "restoration" tray series and/or for the "normal" orthodontic tray series. These simulations can be shown in a side-by-side comparison or they can be shown separately. The restoration tray simulation can be accompanied with a dental restoration simulation (e.g., at the same time as or subsequent to the restoration tray series simulation). Such comparisons can desirably allow doctors and patients to be better informed when deciding which treatment path to take. The different timing and/or costs of these different treatment options can also be simulated (e.g., visually displayed), which can further help doctors and patients decide which treatment path to take.

Method of Use

Figure 5:
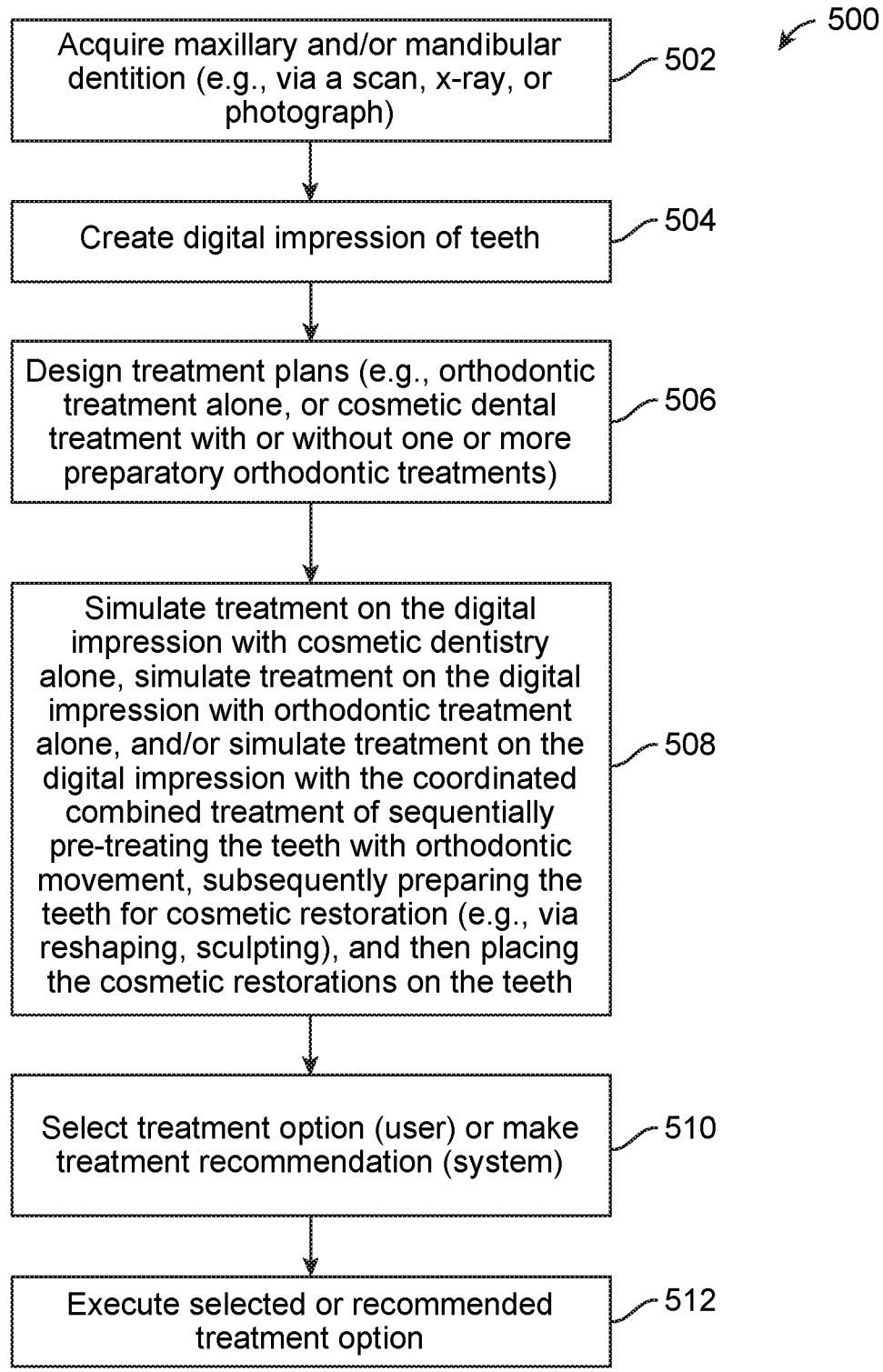
FIG. 5 illustrates a variation of a process undertaken by the system.

FIG. 5 illustrates a variation of a process 500 that is implementable using and/or performable by the system 100. The method 500 can involve acquiring (e.g., detecting and/or observing, for example, scanning, x-raying, photographing) the maxillary and/or mandibular dentition with one or more data acquisition devices 102 in operation 502.

The method 500 can further involve creating a digital impression of the dentition in operation 504 from the data acquired in operation 502.

The method 500 can further involve designing treatment plans in operation 506 (e.g., orthodontic treatment alone, or cosmetic dental treatment with or without one or more preparatory orthodontic treatments). The treatment plans designed can depend on, for example, the presence and extent of any malocclusions and/or the bounds and relative positions of the teeth.

The method 500 can further involve simulating the different treatment options in operation 508, for example, simulating orthodontic movement of teeth alone, simulating cosmetic restorations alone, and/or simulating the coordinated combined treatment of sequentially first pretreating the teeth with orthodontic movement, subsequently preparing the teeth for cosmetic restoration (e.g., via reshaping, sculpting), and then placing the cosmetic restorations on the teeth (e.g., teeth 200a).

The method 500 can further involve the user (e.g., dentist, orthodontist, patient) selecting a treatment option, and/or the system (e.g., system 100) making a treatment recommendation in operation 510. The treatment recommendation can be one of the options designed in operation 506 and/or simulated in operation 508.

The method 500 can further involve executing the selected or recommended treatment option in operation 512, for example with orthodontic preparatory treatment affected by an orthodontic tray, and the subsequent application of cosmetic restorations to the teeth. Once the decision on which treatment option/protocol is to be used, then the system 100 can design and execute on the orthodontic and cosmetic restoration appliances associated with the selected or recommended treatment.

Figure 6:
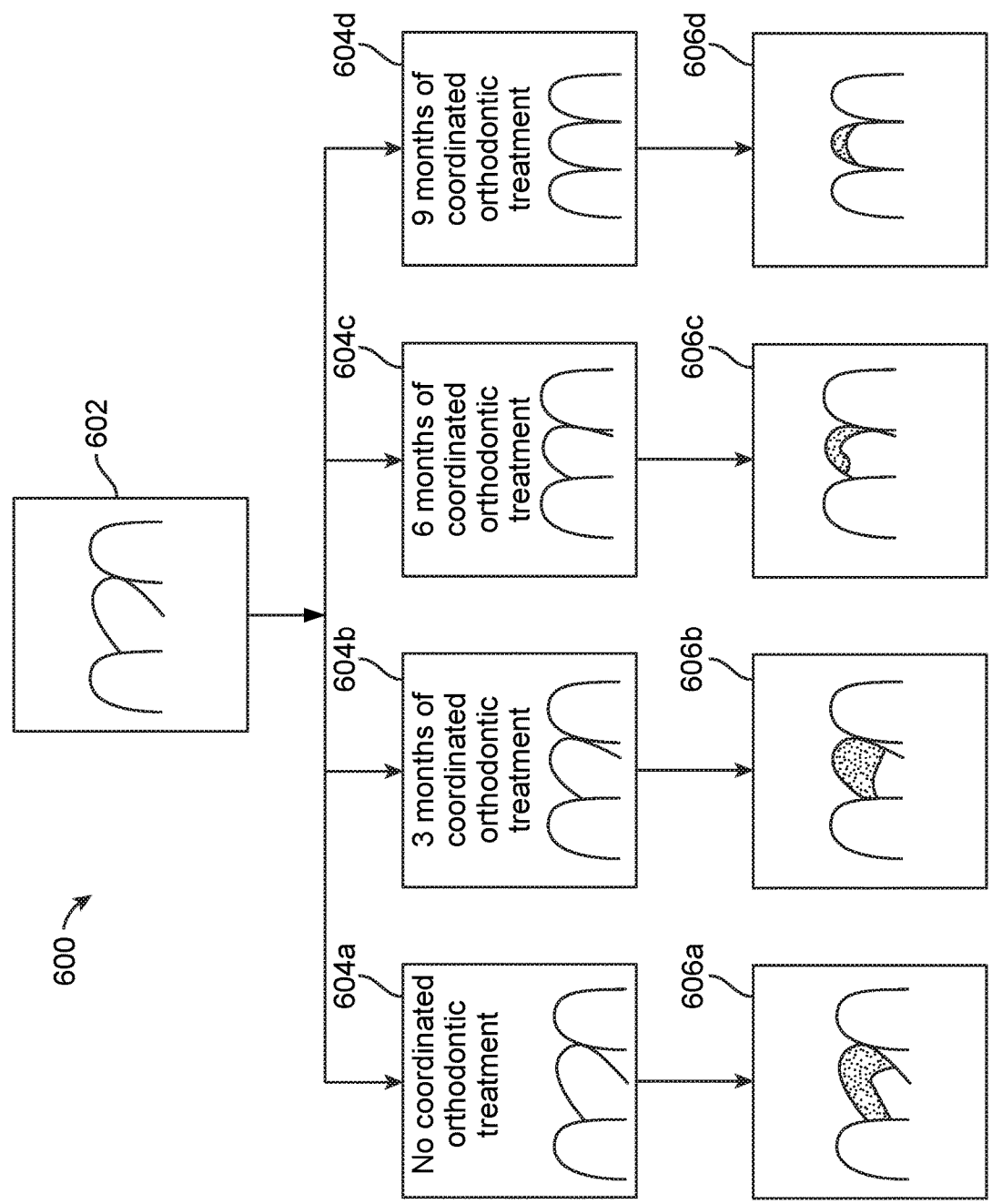
FIG. 6 illustrates a variation of various treatment options being simulated by the system.

FIG. 6 illustrates a variation of various treatment options 600 being simulated by the system. A portion of a digital impression (e.g., 3 teeth) is shown in block 602. Blocks 604a-604d are schematic variations of simulations of no coordinated orthodontic treatment before cosmetic restoration, three months of coordinated orthodontic treatment beforehand, 6 months of coordinated orthodontic treatment beforehand, and 9 months of coordinated orthodontic treatment beforehand, respectively, with the middle tooth progressively moving closer to a more vertical position as the amount of treatment time increases. The orthodontic treatment time can range from zero to about 2 years, including every 1 month increment within this range, for example, 0 months, 3 months, 6 months, 9 months, or 12 months. The number of orthodontic trays used in each of the blocks 604b, 604c, and 604d can vary as described above, with the total number being dependent on the needs of each patient. Blocks 606a-606d are schematic variations of simulations showing the extent of tooth removal (e.g., via reshaping, via sculpting) subsequent to the coordinated orthodontic treatment in blocks 604a-604d, respectively, with amount of tooth removal for the cosmetic restoration progressively becoming less as the amount of orthodontic treatment time increases from 0 months to 12 months (the amount removed is indicated by the shaded regions).

A number of variations have been described. Nevertheless, it will be understood by one of ordinary skill in the art that various modifications may be made without departing from the spirit and scope of the variations. In addition, the flowcharts, logic flows, and algorithms depicted in the figures do not require the particular order shown, or sequential order, to achieve desirable results, and are exemplary only. In addition, other steps or operations may be provided, or steps or operations may be eliminated, from the described flows and algorithms, and other components and/or features may be added to, or removed from, the described and contemplated systems. Accordingly, other variations are within the scope of the following claims.

It will be understood by one of ordinary skill in the art that the various methods and processes disclosed herein may be embodied in a non-transitory readable medium, machine-readable medium, and/or a machine accessible medium comprising instructions compatible, readable, and/or executable by a processor or processing unit of a machine, device, or computing device. The structures and modules in the figures may be shown as distinct and communicating with only a few specific structures and not others. The structures may be merged with each other, may perform overlapping functions, and may communicate with other structures not shown to be connected in the figures. Accordingly, the specification and/or drawings may be regarded in an illustrative rather than a restrictive sense.

The claims are not limited to the exemplary variations shown in the figures, but instead may claim any feature disclosed or contemplated in the disclosure as a whole. Any elements described herein as singular can be pluralized (i.e., anything described as "one" can be more than one). Any species element of a genus element can have the characteristics or elements of any other species element of that genus. Some elements may be absent from individual figures for reasons of illustrative clarity. The above-described configurations, elements or complete assemblies and methods and their elements for carrying out the disclosure, and variations of aspects of the disclosure can be combined and modified with each other in any combination. All devices, apparatuses, systems, methods, and algorithms described herein can be used for medical (e.g., diagnostic, therapeutic or rehabilitative) or non-medical purposes.

What is claimed is:

1. A method of coordinating orthodontic and cosmetic dental treatments, the method comprising:
    recommending, via a processor, a tooth for restoration;
    determining a first amount of partial tooth destruction of the tooth when the tooth is modeled in a first position;
    determining an amount of cosmetic restoration of the tooth based on the first amount of partial tooth destruction;
    determining a second amount of partial tooth destruction of the tooth when the tooth is modeled in a second position, wherein the first amount of partial tooth destruction is greater than the second amount of partial tooth destruction;
    selecting the first position of the tooth for restoration of the tooth;
    determining and recommending, via the processor before starting treatment, a first orthodontic treatment plan that moves the tooth to the first position along a path specifically tailored to accommodate the amount of cosmetic restoration;
    determining and recommending, via the processor before starting treatment, a second orthodontic treatment plan that moves the tooth to the first position along a different path, arc, and/or angle than the path specifically tailored to accommodate the amount of cosmetic restoration;
    simulating, before starting treatment, the first orthodontic treatment plan and the second orthodontic treatment plan;
    comparing, before starting treatment, the first orthodontic treatment plan with the second orthodontic treatment plan;
    selecting, before starting treatment, the first orthodontic treatment plan;
    preparing the tooth for the amount of cosmetic restoration by orthodontically moving the tooth to the first position along the path specifically tailored to accommodate the amount of cosmetic restoration;
    preparing the tooth for the amount of cosmetic restoration by performing the first amount of partial tooth destruction when the tooth is in the first position; and
    cosmetically restoring the tooth by performing the amount of cosmetic restoration, wherein the higher the degree of partial correction, the lower the amount of destruction of the tooth that is required prior to placement of a dental restoration.

2. A method of coordinating orthodontic and cosmetic dental treatments, the method comprising:
    identifying, via a processor, a candidate tooth for orthodontic repositioning and for cosmetic dental restoration;
    designing, via the processor based on the candidate tooth identified, a first orthodontic treatment plan for the candidate tooth and a second orthodontic treatment plan for the candidate tooth;
    designing, via the processor based on the candidate tooth identified, a first cosmetic dental treatment plan for the candidate tooth, wherein the first cosmetic dental treatment plan is associated with the first orthodontic treatment plan;
    designing, via the processor based on the candidate tooth identified, a second cosmetic dental treatment plan for the candidate tooth, wherein the second cosmetic dental treatment plan is associated with the second orthodontic treatment plan;
    simulating the first orthodontic treatment plan, the first cosmetic dental treatment plan, the second orthodontic treatment plan, and the second cosmetic dental treatment plan on an electronic display, wherein simulating the first orthodontic treatment plan and the first cosmetic dental treatment plan comprises simulating a first orthodontic path for the candidate tooth identified and a first type of cosmetic restoration treatment product, wherein simulating the second orthodontic treatment plan and the second cosmetic dental treatment plan comprises simulating a second orthodontic path for the candidate tooth identified and a second type of cosmetic restoration treatment product different from the first type of cosmetic restoration treatment product, wherein the first orthodontic path for the candidate tooth identified is different than the second orthodontic path for the candidate tooth identified, and wherein a final tooth position of the candidate tooth identified is the same at the end of the first orthodontic path and at the end of the second orthodontic path;
    determining and comparing a first amount of destruction of the candidate tooth with a second amount of destruction of the candidate tooth, wherein the first amount of destruction is associated with the first type of cosmetic restoration treatment product, wherein the second amount of destruction is associated with the second type of cosmetic restoration treatment product, wherein the first amount of destruction is greater than the second amount of destruction;
    recommending, via the processor, the first orthodontic treatment plan and the first cosmetic dental restoration treatment plan or the second orthodontic treatment plan and the second cosmetic dental restoration treatment plan for the candidate tooth, wherein the recommendation is selectable by the user;
    executing the orthodontic treatment plan recommended by the processor, wherein executing the orthodontic treatment plan recommended by the processor comprises preparing the candidate tooth for the first amount of destruction or the second amount of destruction by orthodontically moving the candidate tooth according to the orthodontic treatment plan recommended by the processor;

after executing the orthodontic treatment plan recommended by the processor, performing the first amount of destruction in preparation for the first cosmetic dental restoration treatment plan or performing the second amount of destruction in preparation for the second cosmetic dental restoration treatment plan recommended by the processor; and after performing the first amount of destruction in preparation for the first cosmetic dental restoration treatment plan or performing the second amount of destruction in preparation for the second cosmetic dental restoration treatment plan recommended by the processor, executing the first cosmetic dental restoration treatment plan or the second cosmetic dental restoration treatment plan recommended by the processor.

3. The method of claim 2, wherein preparing the candidate tooth for the second amount of destruction by orthodontically moving the candidate tooth takes longer than preparing the candidate tooth for the first amount of destruction by orthodontically moving the candidate tooth.

4. The method of claim 1, further comprising simulating the first orthodontic treatment plan side-by-side with the second orthodontic treatment plan.

5. The method of claim 1, further comprising simulating the cost of the first orthodontic treatment plan and the cost of the second orthodontic treatment plan.

6. The method of claim 1, wherein a portable device comprises the processor.

7. The method of claim 6, wherein the portable device comprises a smartphone.

8. The method of claim 2, wherein the first type of cosmetic restoration treatment product comprises a bonding, and wherein the second type of cosmetic restoration treatment product comprises a veneer or a crown.

9. The method of claim 2, wherein the first type of cosmetic restoration treatment product comprises a veneer, and wherein the second type of cosmetic restoration treatment product comprises a bonding or a crown.

10. The method of claim 2, wherein the user comprises a patient.

11. The method of claim 2, wherein the user comprises a dentist, an orthodontist, or a patient.

* * * * *